(12) United States Patent
Thakur

(10) Patent No.: US 9,150,589 B2
(45) Date of Patent: Oct. 6, 2015

(54) POLYMORPHOUS FORMS III AND IV OF N-BENZOYL—STAUROSPORINE

(75) Inventor: Ranjit Thakur, Basel (CH)

(73) Assignee: NOVARTIS AG, Basel (CH)

( * ) Notice: Subject to any disclaimer, the term of this patent is extended or adjusted under 35 U.S.C. 154(b) by 494 days.

(21) Appl. No.: 13/512,398

(22) PCT Filed: Nov. 29, 2010

(86) PCT No.: PCT/EP2010/068359
§ 371 (c)(1),
(2), (4) Date: May 29, 2012

(87) PCT Pub. No.: WO2011/064355
PCT Pub. Date: Jun. 3, 2011

(65) Prior Publication Data
US 2012/0245160 A1   Sep. 27, 2012

(30) Foreign Application Priority Data
Nov. 30, 2009  (EP) .................................... 09177490

(51) Int. Cl.
*C07D 498/22* (2006.01)

(52) U.S. Cl.
CPC .................. *C07D 498/22* (2013.01)

(58) Field of Classification Search
None
See application file for complete search history.

(56) References Cited

U.S. PATENT DOCUMENTS 5,093,330 A  *  3/1992  Caravatti et al.  .........  514/211.08

FOREIGN PATENT DOCUMENTS

| EP | 0 296 110 A2 | 12/1998 |
| JP | 05 247055 A | 9/1993 |
| JP | 1993-247055 | 9/1993 |
| WO | WO 2005/089718 A2 | 9/2005 |
| WO | WO 2006/048296 A1 | 5/2006 |
| WO | WO 2008/021347 A2 | 2/2008 |

OTHER PUBLICATIONS

Martin Muller et al., 2000, "Experimental Study of the Effect of Process Parameters in the Recrystallization of an Organic Compound Using Compressed Carbon Dioxide as Antisolvent", Ind. Eng. Chem. Res. 39:2260-2268.

Nakai et al., Shin-seiyakugaku, Nanzan-do, vol. 1, pp. 102 and 103, (Nov. 25, 1982) (English Translation).

Shioji et al., "A manufacturing technology for solids formulations", CMC publishing company, (trade edition), pp. 9, pp. 12, pp. 13, (Jan. 27, 2003) (English Translation).

Matsuoka, Masakuni, "Advanced Crystallization Technology of Organic Materials-Control of Size, Morphology, Polymoroph and Purity", Pharm Tech Japan, vol. 19, No. 9, pp. 91(955)-101(965), (May 1, 2003) (English Abstract Summary).

Yamamoto et al., "crystal polymorph and separate operation", Separation Process Engineering, vol. 25, No. 5, pp. 9(381)-38(410), (Oct. 5, 1995) English Abstract Summary.

Takada et al., "API form screening and selection in drug discovery stage", Pharm Stage, vol. 6, No. 10, pp. 20-25, (Jan. 15, 2007) (English Translation).

"Guidelines for residual solvent of pharmaceuticals", pp. 1-11, (1998) ( English Abstract Summary)

Jorg Breitenbach, "Melt extrusion: from process to drug delivery technology", European Journal of Pharmaceutics and Biopharmaceutics, vol. 54, pp. 107-117, 2002.

* cited by examiner

*Primary Examiner* — Noble Jarrell
(74) *Attorney, Agent, or Firm* — Mehdi Ganjeizadeh

(57) ABSTRACT

The present invention relates to a crystalline form III and a crystalline form IV of N-benzoyl staurosporine. N-benzoyl staurosporine is also known as Midostaurin or PKC412.

10 Claims, 4 Drawing Sheets

POLYMORPHOUS FORMS III AND IV OF N-BENZOYL—STAUROSPORINE

This application is a National Stage of International Application No. PCT/EP2010/068359 filed Nov. 29, 2012, which claims benefit of European Application 09177490.1 filed Nov. 30, 2009, the entire disclosures of which are herein incorporated.

The present invention relates to new crystalline forms of N-benzoyl staurosporine, and a process for the preparation of these crystalline forms.

Protein kinase C, herein after abbreviated as PKC, is one of the key enzymes in cellular signal transduction pathways, and it has a pivotal role in the control of cell proliferation and differentiation. PKC is a family of serine/threonine kinases.

At least 12 isoforms of PKC have been identified, and they are commonly divided into three groups based on their structure and substrate requirements. Promising results have recently been achieved in clinical trials investigating the effects of the protein tyrosine kinase inhibitor PKC412 on AML patients harboring mutations in the FLT3 protein.

Midostaurin is N-[(9S,10R,11R,13R)-2,3,10,11,12,13-hexahydro-10-methoxy-9-methyl-1-oxo-9,13-epoxy-1H, 9H-diindolo[1,2,3-gh:3',2',1'-lm]pyrrolo[3,4-j][1,7]benzodiazonin-11-yl]-N-methylbenzamide of the following formula:

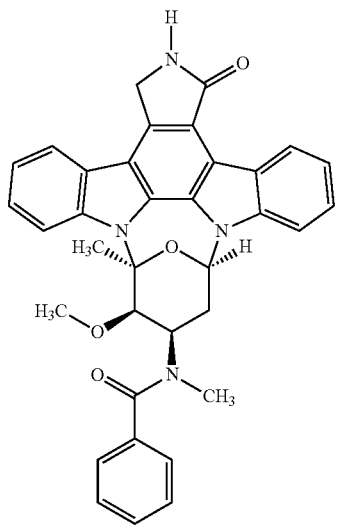 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4]

Midostaurin [International Nonproprietary Name] is also known as N-benzoyl staurosporine or PKC412.

N-benzoyl staurosporine is a derivative of the naturally occurring alkaloid staurosporine, and has been specifically described in the European Patent No. 0 296 110, U.S. Pat. No. 5,093,330.

In WO 2006/048296, a crystalline form II of N-benzoyl staurosporine is disclosed. The melting point of this compound is of about 260° C. as disclosed in WO 2008/021347.

Many poorly water soluble therapeutic compounds such as N-benzoyl staurosporine exist in a physical state that is highly crystalline. Additionally, such high crystalline therapeutic compounds often have high melting points. Thus, it would be of interest to provide N-benzoyl staurosporine in a state which allows for both greater solubility and faster dissolution of the therapeutic compound, thereby increasing bioavailability of the drug.

Of particular interest is melt extrusion which uses a twin screw extruder to combine a therapeutic compound with an inert carrier to form a solid dispersion having improved solubility and dissolution. Typically, the twin screw extruder is heated to facilitate mixing of the therapeutic compound with the carrier.

As indicated above, the crystalline forms of N-benzoyl staurosporine known so far have quite high melting points. Furthermore, the melting points of these polymorphs are close to the decomposition temperature of N-benzoyl staurosporine which makes their use in melt extrusion for the preparation of pharmaceutical compositions difficult.

Thus, considering the drawbacks outlined above, it is an object of the present invention to provide crystalline N-benzoyl staurosporine in a form which is useful for the preparation of pharmaceutical compositions by melt extrusion. In particular, the new crystalline form of N-benzoyl staurosporine should minimize the risk of decomposition during melt extrusion.

According to a first aspect of the present invention, the problem is solved by providing a first crystalline form of N-benzoyl staurosporine (in the following referred to as crystalline form III), which shows on X-ray diffraction peaks at an angle of refraction 2theta of 5.3, 6.9, 7.9, 15.9±0.2°. The X-ray diffraction diagram is measured on a powder sample with Cu Kα radiation (Kα1 radiation, wavelength λ=1.54060 Å).

The crystalline form III of N-benzoyl staurosporine has a melting point which is significantly lower than the melting points of crystalline N-benzoyl staurosporine modifications described so far in the prior art. In other words, for crystalline form III, the decomposition temperature is significantly higher than the melting temperature. Thus, intimate mixing of crystalline form III with pharmaceutically acceptable excipients during melt extrusion can be accomplished at lower temperature while simultaneously reducing the risk of decomposition.

Preferably, the crystalline form III additionally shows on X-ray diffraction peaks at an angle of refraction 2theta of 5.3, 6.9, 7.9, 13.7, 15.9, 18.7, 20.1±0.2°.

Even more preferably, the crystalline form III of benzoyl staurosporine shows an X-ray diffraction pattern with diffraction peaks as listed below in Table 1.

TABLE 1

| Peak position 2θ (deg) | d-spacing (Å) | Relative intensity (%) |
| --- | --- | --- |
| 5.3 | 16.69 | medium |
| 6.9 | 12.88 | strong |
| 7.9 | 11.16 | medium |
| 8.7 | 10.15 | medium |
| 9.5 | 9.34 | medium |

TABLE 1-continued

| Peak position 2θ (deg) | d-spacing (Å) | Relative intensity (%) |
|---|---|---|
| 10.1 | 8.75 | medium |
| 11.2 | 7.91 | weak |
| 12.1 | 7.34 | medium |
| 13.7 | 6.46 | medium |
| 14.0 | 6.31 | medium |
| 15.9 | 5.57 | medium |
| 17.6 | 5.04 | medium |
| 18.7 | 4.73 | medium |
| 20.1 | 4.41 | medium |
| 21.4 | 4.14 | weak |
| 23.1 | 3.85 | weak |
| 23.8 | 3.74 | weak |
| 25.0 | 3.57 | weak |
| 26.0 | 3.43 | weak |

As known by the skilled person, d-spacing values can be calculated from Bragg's law. Relative intensities were determined by comparing peak heights. The relative intensities can vary from sample to sample due to the so-called preferred orientation effect.

Figure 1:
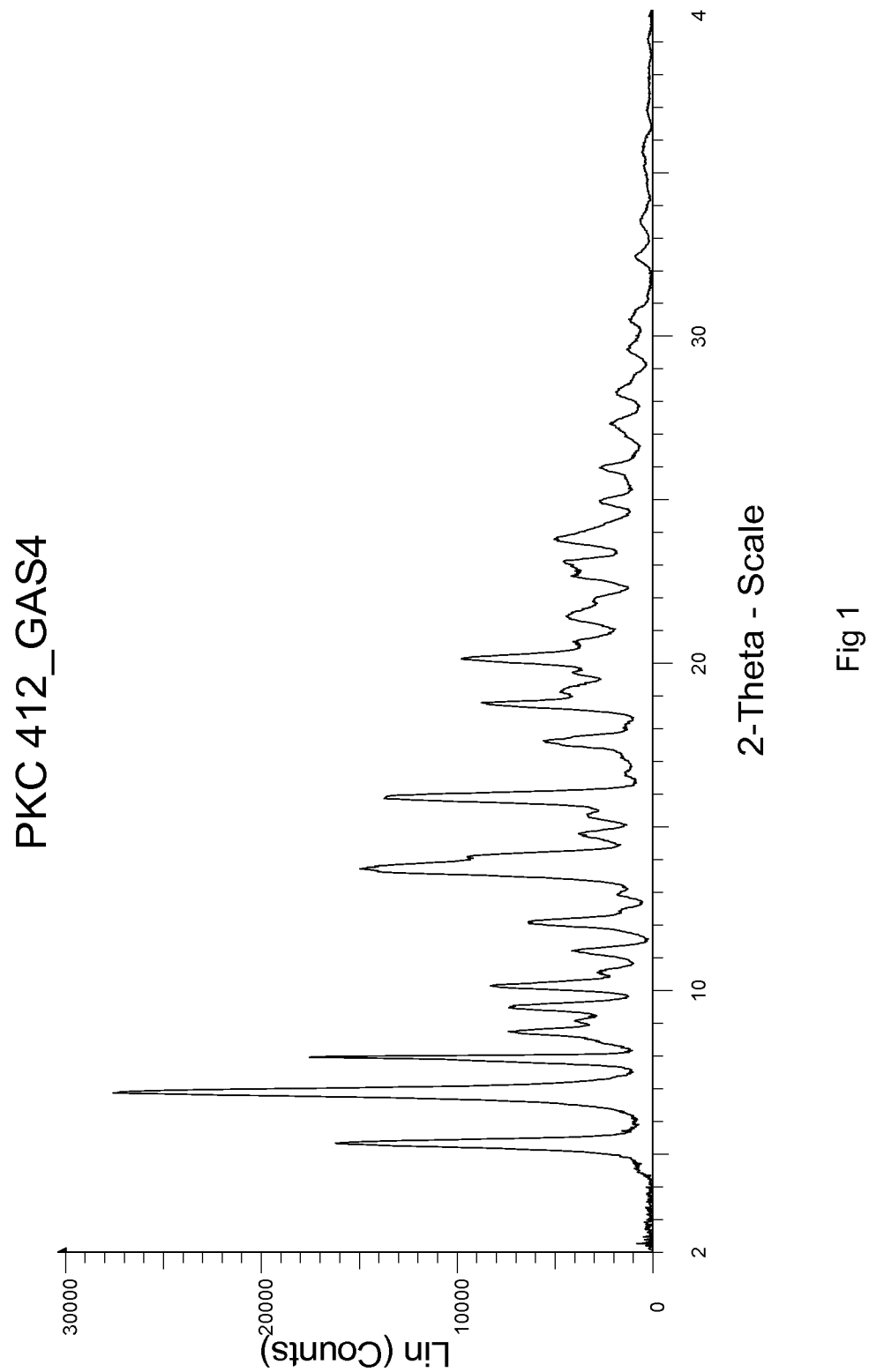
FIG. 1 shows X-ray diffractograms of the crystalline form III of N-benzoyl staurosporine.

In a preferred embodiment, the crystalline form III of N-benzoyl staurosporine has substantially the same X-ray diffraction pattern as shown in FIG. 1.

Figure 2:
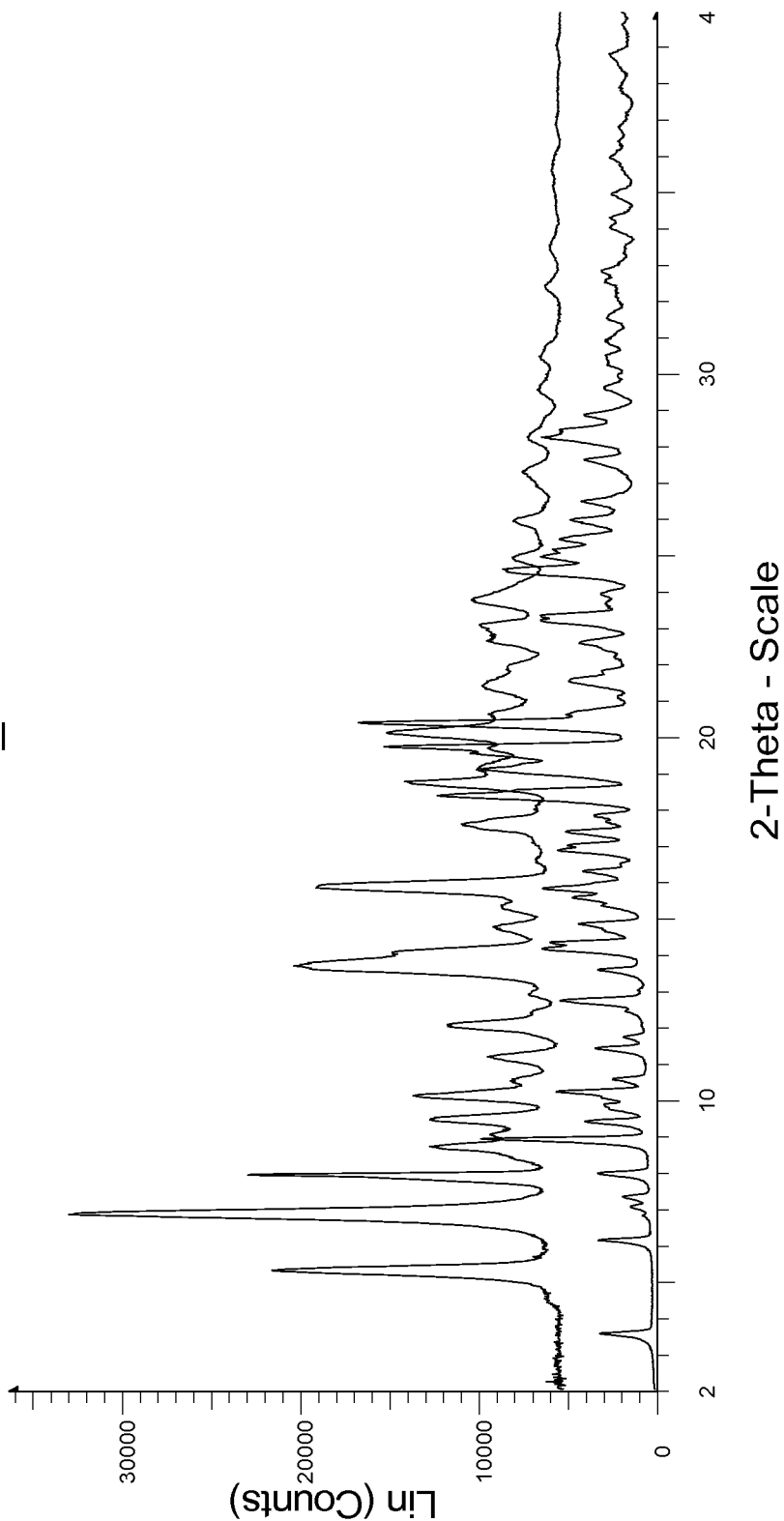
FIG. 2 shows X-ray diffractograms of the crystalline form III of N-benzoyl staurosporine and the crystalline form II of N-benzoyl staurosporine as disclosed in WO 2006/048296 (top form III, bottom crystalline form II).

FIG. 2 shows X-ray diffractograms of the crystalline form III of the present invention and the crystalline form II as disclosed in WO 2006/048296.

Preferably, the crystalline form III has a melting point Tm, measured by differential scanning calorimetry DSC, of 206±10° C.

The crystalline form III decomposes above 270° C., when heated with a heating rate of 20K/min under nitrogen atmosphere.

The crystalline form III contains about 3.2% of residual solvents or water which evaporate upon heating at about 11° C.

In the present invention, the term "solvate" is to be interpreted according to its commonly accepted meaning, i.e. it refers to solvent molecules which are incorporated into the crystalline structure of the "host" (N-benzoyl staurosporine in the present case).

According to a second aspect of the present invention, the problem is solved by providing a second crystalline form of N-benzoyl staurosporine (in the following referred to as crystalline form IV), which shows on X-ray diffraction peaks at an angle of refraction 2theta of 10.0, 12.0, 15.8±0.2°.

The X-ray diffraction diagram is measured on a powder sample with Cu Kα radiation (Kα1 radiation, wavelength λ=1.54060 Å).

Like the crystalline form III the crystalline form IV of N-benzoyl staurosporine has a melting point which is significantly lower than the melting points of crystalline N-benzoyl staurosporine modifications described so far in the prior art. In other words, for crystalline form IV, the decomposition temperature is significantly higher than the melting temperature.

Intimate mixing of crystalline form IV with pharmaceutically acceptable excipients during melt extrusion can be accomplished at lower temperature while simultaneously reducing the risk of decomposition.

Preferably, the crystalline form IV additionally shows on X-ray diffraction peaks at an angle of refraction 2theta of 7.9, 10.0, 12.0, 12.9, 13.5, 15.8, 17.8±0.2°.

Even more preferably, the crystalline form IV of benzoyl staurosporine shows an X-ray diffraction pattern with diffraction peaks as listed in Table 2

TABLE 2

| Peak position 2θ (deg) | d-spacing (Å) | Relative intensity (%) |
|---|---|---|
| 6.5 | 13.61 | weak |
| 7.9 | 11.19 | strong |
| 10.0 | 8.81 | weak |
| 12.0 | 7.39 | medium |
| 12.9 | 6.84 | medium |
| 13.5 | 6.53 | medium |
| 15.8 | 5.62 | medium |
| 17.6 | 5.05 | medium |

As known by the skilled person, d-spacing values can be calculated from Bragg's law. Relative intensities were determined by comparing peak heights. Relative intensities can vary from sample to sample due to the so-called preferred orientation effect.

Figure 3:
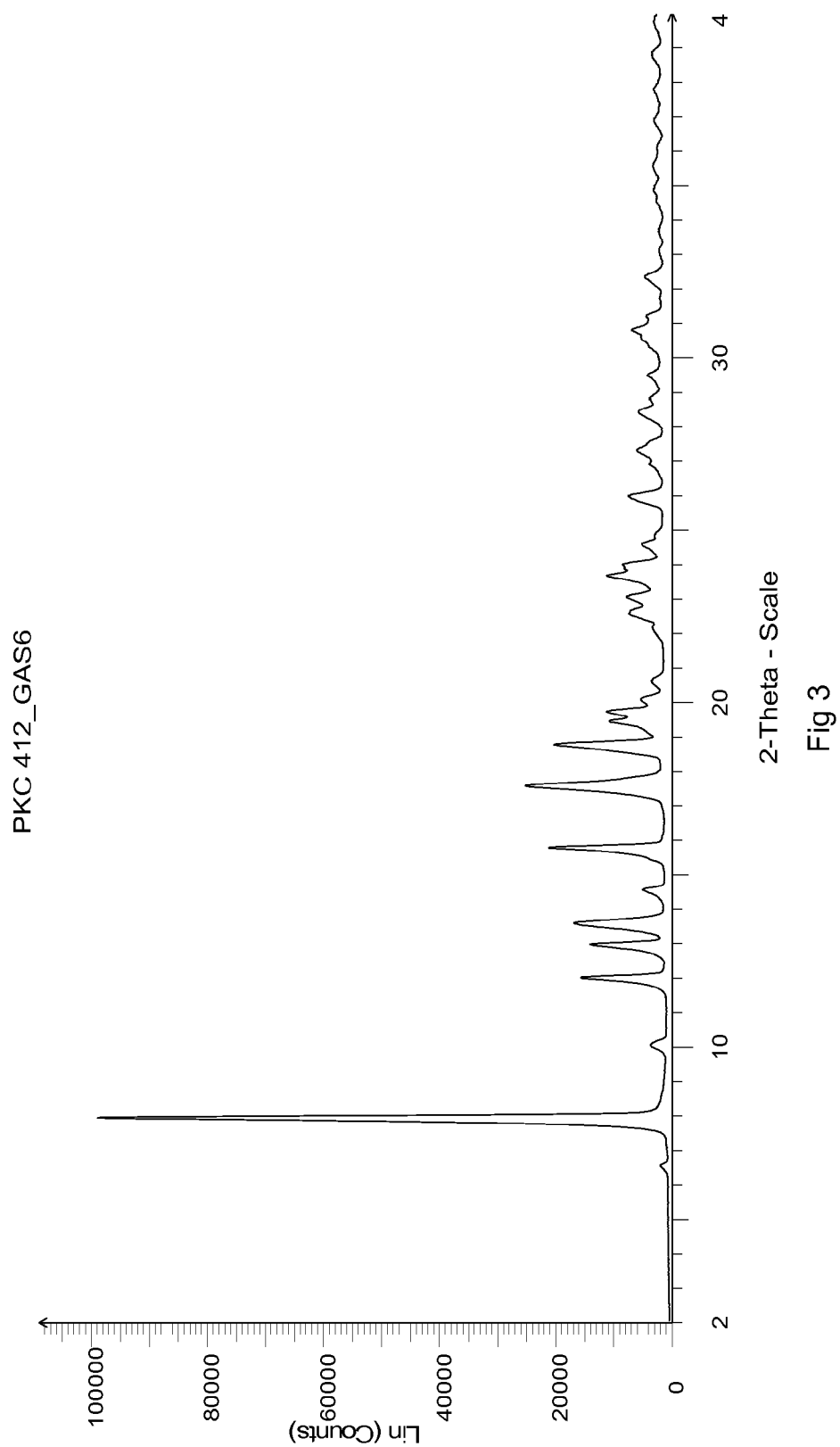
FIG. 3 shows X-ray diffractograms of the crystalline form IV of N-benzoyl staurosporine.

In a preferred embodiment, the crystalline form IV of N-benzoyl staurosporine has substantially the same X-ray diffraction pattern as shown in FIG. 3.

Figure 4:
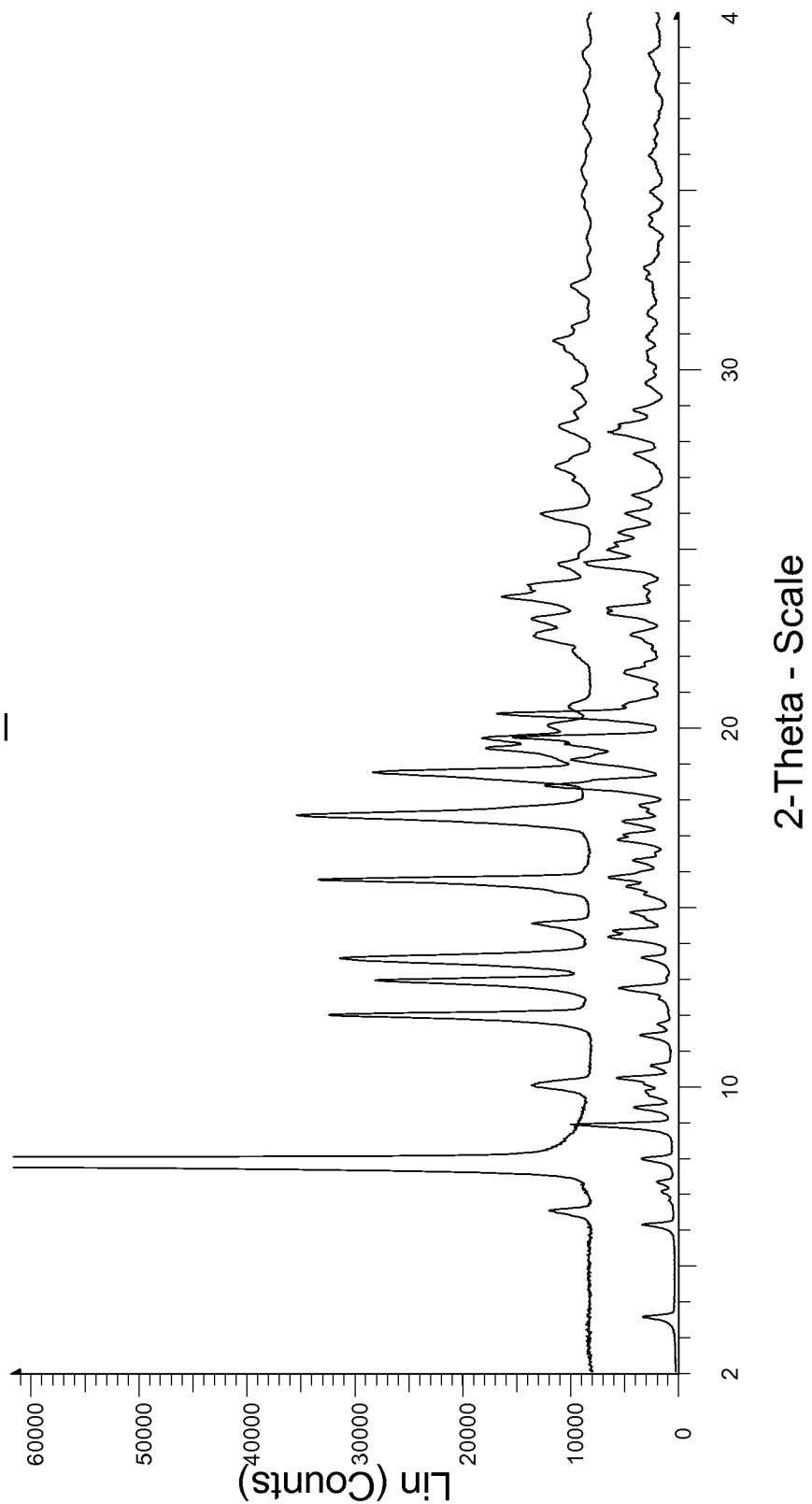
FIG. 4 shows X-ray diffractograms of the crystalline form IV of N-benzoyl staurosporine and the crystalline form II of N-benzoyl staurosporine as disclosed in WO 2006/048296.

FIG. 4 shows X-ray diffractograms of the crystalline form IV of the present invention and the crystalline form II as disclosed in WO 2006/048296.

Preferably, the crystalline form IV has a melting point Tm, measured by differential scanning calorimetry DSC, of 215±10. ° C.

The crystalline form IV decomposes at about 270° C. when heated at 20K/min under nitrogen atmosphere.

The crystalline form III contains 6.2% residual solvents or water which evaporate upon heating at about 91° C.

In the present invention, the term "solvate" is to be interpreted according to its commonly accepted meaning, i.e. it refers to solvent molecules which are incorporated into the crystalline structure of the "host" (N-benzoyl staurosporine in the present case).

The present invention also provides a process for the preparation of crystalline N-benzoyl staurosporine, e.g. crystalline form III or crystalline form IV, comprising the following steps:

(i) providing in a crystallinelization vessel a solution of N-benzoyl staurosporine in acetonitrile or tetrahydrofuran (ii) adding compressed carbon dioxide to the solution in the crystallinelization vessel at a process temperature Tp, and (iii) separating the precipitated crystalline N-benzoyl staurosporine from the crystallinelization vessel.

The crystallinelization vessel may be any vessel or container which can be used at elevated pressure. It may be part of another vessel (pressure vessel) which is specifically adapted to be operated under increased pressure. However, such vessels are known to the skilled person.

Preferably, the concentration of N-benzoyl staurosporine in the solution prepared in step (i) is from 1 mg/ml to 50 mg/ml, more preferably 5 mg/ml to 20mg/ml of the solubility at the process temperature Tp.

Preferably, amorphous N-benzoyl staurosporine is dissolved in tetrahydrofuran so as to obtain the solution of step (i). The preparation of amorphous N-benzoyl staurosporine is described e.g. in WO 2006/048296. However, other known forms of N-benzoyl staurosporine can be used as well, e.g. the crystalline forms disclosed in WO 2006/048296.

In step (ii), compressed carbon dioxide is introduced into the solution of N-benzoyl staurosporine in THF. In the present invention, the term "compressed" refers to any carbon dioxide having a pressure higher than atmospheric pressure. Preferably, the pressure of the compressed carbon dioxide is within the range of 6 MPa to 12 MPa, more preferably 7 MPa to 9 MPa. More preferably, the compressed carbon dioxide is in a supercritical state. In the present invention, the term "supercritical" is to be interpreted according to its commonly accepted meaning, i.e. it refers to carbon dioxide at a temperature and pressure above its critical point.

In the process of the present invention, the compressed carbon dioxide, preferable the supercritical carbon dioxide acts as an anti-solvent for the solute (i.e. N-benzoyl staurosporine) which is initially solubilized in the THF solvent. The solution of step (i) is expanded by adding compressed carbon dioxide. Due to the volumetric expansion of the solution, solubility of N-benzoyl staurosporine in THF is reduced.

Such a type of process is also referred to as GAS (gas antisolvent) recrystallinelization. General information about GAS recrystallinelization can be found e.g. in Ind. Eng. Chem. Res. 2000, 39, pp. 2260-2268, M. Müller et al.; and J. of Supercritical Fluids, 27 (2003), pp. 195-203, M. Mazzotti et al.

Preferably, the formation of either crystalline form III or crystalline form IV is controlled by selecting appropriate temperature and pressure conditions.

In a preferred embodiment for the preparation of crystalline form III, the process temperature Tp of step (ii) is within the range of 20° C. to 60° C., more preferably 23° C. to 45° C. so as to obtain precipitated crystalline N-benzoyl staurosporine of crystalline form III, upon adding compressed carbon dioxide.

In a preferred embodiment for the preparation of crystalline form IV, the process temperature Tp of step (ii) is within the range of 20° C. to 60° C., more preferably 23° C. to 45° C. upon adding compressed carbon dioxide.

Preferably, the compressed carbon dioxide is fed to the solution at a flow rate within the range of 1 ml/min to 20 ml/min, more preferably 1 ml/min to 5 ml/min.

In the process of the present invention, it may be preferred that, after precipitation of the crystalline N-benzoyl staurosporine, an outlet valve of the crystallinelization vessel is opened, the crystallinelization vessel is purged with carbon dioxide and subsequently depressurized, and the crystalline N-benzoyl staurosporine is separated from the crystallinelization vessel.

Preferably, the purging step is continued for a sufficient period in time so as to obtain a solvent-free, more preferably a solvate-free crystalline form of N-benzoyl staurosporine.

According to another aspect, the present invention provides a pharmaceutical composition, comprising the crystalline form III of N-benzoyl staurosporine as described above and/or the crystalline form IV of N-benzoyl staurosporine as described above, and at least one pharmaceutically acceptable excipient.

Tablets or gelatin capsules containing the active substance together with diluents, e.g., lactose, dextrose, sucrose, mannitol, sorbitol, cellulose and/or glycerin; and/or lubricants, e.g., silica, talc, stearic acid or salts thereof, typically magnesium or calcium stearate; and/or PEG, are preferably used for oral administration. Tablets may likewise contain binders, e.g., magnesium aluminum silicate, starches, typically corn, wheat or rice starch, gelatin, methylcellulose, sodium carboxymethylcellulose and/or polyvinylpyrrolidone; and, if so desired, disintegrants, e.g., starches, agar, alginic acid or a salt thereof, typically sodium alginate; and/or effervescent mixtures, or adsorbents, coloring agents, flavors and sweetening agents.

If the pharmaceutical composition is prepared by a process which comprises a melt extrusion step, it preferably comprises a pharmaceutically acceptable matrix polymer in which the therapeutic compound is dispersed. Preferred types of polymers include, but are not limited to, water-soluble, water-swellable, water insoluble polymers and combinations of the foregoing.

Examples of polymers include, but are not limited to:

homopolymers and copolymers of N-vinyl lactams, e.g., homopolymers and copolymers of N-vinyl pyrrolidone (e.g. polyvinylpyrrolidone), copolymers of N-vinyl pyrrolidone and vinyl acetate or vinyl propionate;

cellulose esters and cellulose ethers (e.g. methylcellulose and ethylcellulose) hydroxyalkylcelluloses (e.g. hydroxypropylcellulose), hydroxyalkylalkylcelluloses (e.g. hydroxypropylmethylcellulose), cellulose phthalates (e.g. cellulose acetate phthalate and hydroxylpropylmethylcellulose phthalate) and cellulose succinates (e.g. hydroxypropylmethylcellulose succinate or hydroxypropylmethylcellulose acetate succinate);

high molecular polyalkylene oxides such as polyethylene oxide and polypropylene oxide and copolymers of ethylene oxide and propylene oxide;

polyacrylates and polymethacrylates (e.g. methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates));

polyacrylamides;

vinyl acetate polymers such as copolymers of vinyl acetate and crotonic acid, partially hydrolyzed polyvinyl acetate;

polyvinyl alcohol; and oligo- and polysaccharides such as carrageenans, galactomannans and xanthan gum, or mixtures of one or more thereof.

Preferably, the pharmaceutical composition as defined above is for the treatment of various diseases, especially cancer or tumor, e.g. leukemias, e.g. acute myeloblastic leukemia, e.g. myeloplastic syndromes, e.g. mastocytosis, inflammatory diseases, bacterial diseases, and arteriosclerosis and various diseases of the cardiovascular system and the central nervous system.

According to a further aspect, the present invention provides the use of crystalline form III and/or crystalline form IV of N-benzoyl staurosporine for the preparation of a medicament for the treatment of various diseases, especially cancer or tumor, e.g. leukemias, e.g. acute myeloblastic leukemia, e.g. myeloplastic syndromes, e.g. mastocytosis, inflammatory diseases, bacterial diseases, and arteriosclerosis and various diseases of the cardiovascular system and the central nervous system.

According to a further aspect, the present invention provides the use of the crystalline form III of N-benzoyl staurosporine as described above and/or the crystalline form IV of N-benzoyl staurosporine as described above for the preparation of a pharmaceutical composition by melt extrusion.

The present invention is now described in further detail by the examples.

EXAMPLES

Measuring Methods

X-Ray Diffraction

X-ray diffractograms of crystalline forms III and IV were measured using a Bruker D8 Diffractometer with Cu Kα1 radiation.

Melting Point

Melting point was measured by differential scanning calorimetry (DSC) using a Mettler DSC822e, a heating rate of 10K/min and sample mass was 2-3 mg.

Example 1

In Example 1, crystalline form III of N-benzoyl staurosporine was prepared by GAS recrystallinelization. The X-ray diffractogram of crystalline form III is shown in FIG. 1 and the X-ray diffractogram of crystalline form III and crystalline form II as disclosed in WO 2006/048296 is shown in FIG. 2.

Example 2

In Example 2, crystalline form IV of N-benzoyl staurosporine was prepared by GAS recrystallinelization. The X-ray diffractogram of crystalline form IV is shown in FIG. 3 and the X-ray diffractogram of crystalline form IV and crystalline form II as disclosed in WO 2006/048296 is shown in FIG. 4.

The invention claimed is:

1. A crystalline form III of N-benzoyl staurosporine, which shows on X-ray diffraction peaks at a wavelength of 1.54060 Å at an angle of refraction 2theta of 5.3, 6.9, 7.9, 15.9±0.2°.

2. The crystalline form III according to claim 1, additionally showing on X-ray diffraction peaks at a wavelength of 1.54060 Å at an angle of refraction 2theta of 5.3, 6.9, 7.9, 13.7, 15.9, 18.7, 20.1±0.2°.

3. The crystalline form III according to claim 1, having a melting point Tm, measured by differential scanning calorimetry DSC, of 206±10° C.

4. A process for the preparation of crystalline III of N-benzoyl staurosporine, comprising the following steps:
  (i) providing in a crystallization vessel a solution of N-benzoyl staurosporine in tetrahydrofuran
  (ii) adding compressed carbon dioxide to the solution in the crystallization vessel at a process temperature Tp, wherein the process temperature is within the range of 20° C. to 60° C. and
  (iii) separating the precipitated crystalline N-benzoyl staurosporine from the crystallinelization vessel.

5. The process according to claim 4, wherein the concentration of N-benzoyl staurosporine in the solution prepared in step (i) is from 1 mg/ml to 50 mg/ml of the solubility at the process temperature Tp.

6. The process according to claim 4, wherein amorphous N-benzoyl staurosporine is dissolved in tetrahydrofuran so as to obtain the solution of step (i).

7. The process according to claim 4, wherein the compressed carbon dioxide is in a supercritical state.

8. The process according to claim 4, wherein the process temperature Tp of step (ii) is within the range of 20° C. to 60° C.

9. The process according to claim 4, wherein the process temperature Tp of step (ii) is within the range of 23° C. to 45° C.

10. A pharmaceutical composition, comprising the crystalline form III of N-benzoyl staurosporine according to claim 1 and at least one pharmaceutically acceptable excipient.

* * * * *